United States Patent
Weiss et al.

(10) Patent No.: US 9,931,464 B2
(45) Date of Patent: Apr. 3, 2018

(54) INJECTION DEVICE FOR ADMINISTERING A LIQUID

(71) Applicant: B. Braun Melsungen AG, Melsungen (DE)

(72) Inventors: Andre Weiss, Guxhagen (DE); Heinz Wiegel, Alheim (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 429 days.

(21) Appl. No.: 14/386,496

(22) PCT Filed: Mar. 20, 2013

(86) PCT No.: PCT/EP2013/055811
§ 371 (c)(1),
(2) Date: Sep. 19, 2014

(87) PCT Pub. No.: WO2013/139852
PCT Pub. Date: Sep. 26, 2013

(65) Prior Publication Data
US 2015/0051546 A1    Feb. 19, 2015

(30) Foreign Application Priority Data

Mar. 20, 2012  (DE) ........................ 10 2012 204 394

(51) Int. Cl.
*A61M 1/00* (2006.01)
*A61M 5/145* (2006.01)
*A61M 5/48* (2006.01)

(52) U.S. Cl.
CPC .......... *A61M 5/1452* (2013.01); *A61M 5/488* (2013.01); *A61M 2205/3337* (2013.01);
(Continued)

(58) Field of Classification Search
CPC .. A61M 5/1452; A61M 5/2459; A61M 5/286; A61M 5/48; A61M 5/482;
(Continued)

(56) References Cited

U.S. PATENT DOCUMENTS 4,331,146 A * 5/1982 Brignola ............... A61M 5/286
604/200
4,731,058 A    3/1988 Doan
(Continued)

FOREIGN PATENT DOCUMENTS

| EP | 1813300 A1 | 8/2007 |
| GB | 2463051 A | 3/2010 |
| WO | 9010468 A1 | 9/1990 |

OTHER PUBLICATIONS

PCT/US2013/055811 International Search Report and Written Opinion; dated Mar. 20, 2013; 4 pages.

*Primary Examiner* — Kevin C Sirmons
*Assistant Examiner* — Leah Swanson
(74) *Attorney, Agent, or Firm* — Reising Ethington P.C.

(57) ABSTRACT

An injection device (10) for administering a liquid has a barrel (12) with an outlet (20) for the liquid, and a piston (14) arranged in the barrel (12). The piston is designed to force the liquid out from the outlet (20) by displacement into the barrel (12). The injection device (10) has an overpressure protection with a sensor (24) and with an actuator (26). The sensor (24) detects the pressure of the liquid in the barrel (12) directly or indirectly. The actuator (26) prevents a further increase in the pressure of the liquid.

11 Claims, 2 Drawing Sheets

Figure 1:
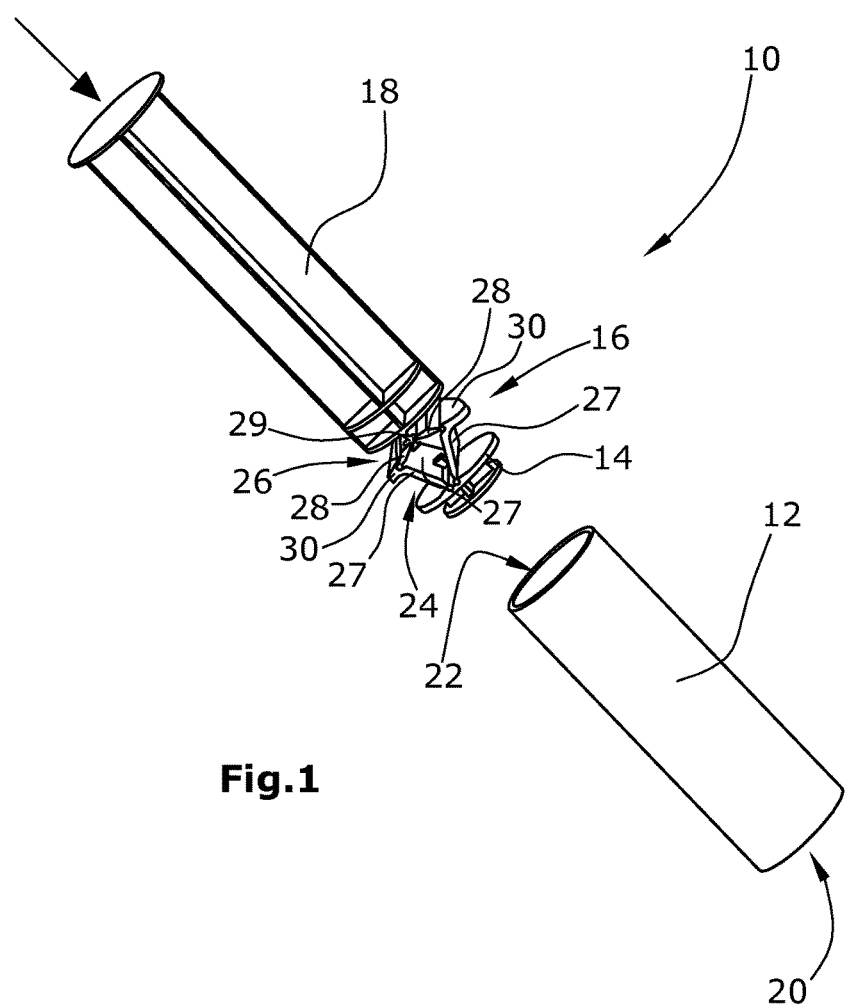

(52) U.S. Cl.
CPC ............... *A61M 2205/3344* (2013.01); *A61M 2205/3355* (2013.01)

(58) Field of Classification Search
CPC ...... A61M 5/484; A61M 5/486; A61M 5/488; A61M 5/31515; A61M 2005/3128; A61M 2005/3132; A61M 2205/344; A61M 2205/3355; A61M 2205/3331; A61M 2205/3334; A61M 2205/3341
USPC .................................................. 604/118, 121
See application file for complete search history.

(56) References Cited

U.S. PATENT DOCUMENTS

| | | |
|---|---|---|
| 4,759,750 A | 7/1988 | DeVries et al. |
| 5,808,203 A | 9/1998 | Nolan et al. |
| 8,622,962 B1* | 1/2014 | Wiley ............... A61M 5/31515 604/110 |

* cited by examiner

INJECTION DEVICE FOR ADMINISTERING A LIQUID

The invention relates to an injection device for administering a liquid.

Injection devices comprising a barrel containing the liquid and an outlet for the liquid are known. When being displaced, a piston arranged in the barrel forces the liquid out of the outlet. For this purpose, a force (actuation pressure) is applied to the piston, by means of which a pressure (liquid pressure) is build up in the liquid contained in the barrel. Such injection devices are typically used in the medical sector, for example as syringes for injecting medicaments or anesthetics. Here, the barrel outlet may be connected with a hollow needle of a syringe, a catheter or any other tube for conducting away the liquid. Moreover, the injection device may serve for filling containers.

In the case of these applications the pressure at which the liquid is forced out of the barrel is often of particular importance. When medicaments or anesthetics are injected into a patient's body, an excessive pressure may lead to physiological damage. For example, an excessive pressure may damage blood vessels, tissue and/or nerves. In particular, in the case of intraneural injection of anesthetics nerves may be damaged at a pressure of more than 20 psi, i. e. more than approximately 1.4 bar. In the case of other applications there is the danger of damage or destruction of filters or a tube system connected with the outlet, such as a balloon catheter for application of stents, for example.

It is an object of the invention to provide an injection device comprising an overpressure protection.

The invention is defined by the features of claim 1.

Accordingly, the injection device comprises an overpressure protection including a sensor directly or indirectly detecting the liquid pressure and an actuator reducing the liquid pressure of the liquid exiting from the outlet, wherein the actuator prevents a further increase in the liquid pressure depending on the liquid pressure detected by the sensor. The sensor can directly detect the liquid pressure, i. e. in the form of a pressure sensor or as a spring element upon which the liquid pressure acts. Alternatively, the sensor can indirectly detect the liquid pressure, for example by directly detecting the actuation pressure acting upon the piston. Here, the actuation pressure acts upon the piston to displace the same and to produce the required liquid pressure at which the liquid is forced out of the outlet. An excessive actuation pressure may result in an excessive liquid pressure. The sensor directly or indirectly detects an excessive liquid pressure and causes the actuator to prevent a further increase in the liquid pressure. The injection device is thus provided with an integrated overpressure protection which detects an excessive pressure in the syringe barrel in an autarchic manner, i.e. independent of the skills of the operator or of external monitoring means, and automatically prevents a further pressure increase.

Here, the sensor is preferably a spring element arranged between the piston and a plunger acting upon the piston. For administering a liquid, the plunger is pushed into the barrel thus exerting an actuation pressure acting upon the piston. The spring element detects in a technically simple manner an excessive pressure acting upon the piston. The spring element indirectly detects the liquid pressure.

The actuator preferably comprises a braking device reducing the advancing rate of the piston relative to the barrel. The braking device is triggered by the sensor. The latter can be defined by a spring element, for example. It is particularly advantageous when the braking device comprises braking elements arranged at the piston and deflected towards the inner wall of the barrel by the actuator. Here, the spring element may comprise two elastically bending flexible springs, in particular spring legs, rigidly connected with the piston and defining the braking elements of the actuator. When an adequate spring force is exceeded, the legs and thus the braking elements of the spring element are deflected towards the inner wall of the barrel. In particular in connection with the spring element this configuration offers a technically simple, durable overpressure protection insusceptible to failure for reducing the liquid pressure. When a critical actuation or liquid pressure is exceeded, a further increase in the liquid pressure is prevented by locking the piston. When subsequently the actuation or liquid pressure is reduced, the sensor can automatically or manually guide the braking elements away from the inner wall of the barrel from inside such that the braking force is reduced and the piston is no longer locked. The overpressure protection is thus reversible.

Alternatively, it is considered that the sensor comprises a pressure sensor, for example a pressure gauge, for measuring the liquid pressure in the barrel or behind the discharge opening of the outlet. Alternatively, the actuator may be a valve, for example a pressure relief valve, arranged at the barrel. When the critical pressure is exceeded, the valve allows liquid to exit from the barrel. The valve may also be a pressure reducing valve arranged downstream of the outlet or a pressure-controlled valve which closes the outlet or a liquid line connected with the outlet when the critical pressure is exceeded.

The overpressure protection and in particular the sensor and the actuator preferably comprise at least one metallic material, such as steel, medical stainless steel, brass, aluminum, gold, silver and/or platinum. Alternatively or additionally, glass, ceramic elements, such as porcelain plugs, and/or plastic materials may be used. Material combinations, such as a holder made of steel with a glass insert for syringe barrels and a piston rod made of steel with plastic sealing rings, are also considered.

Figure 2:
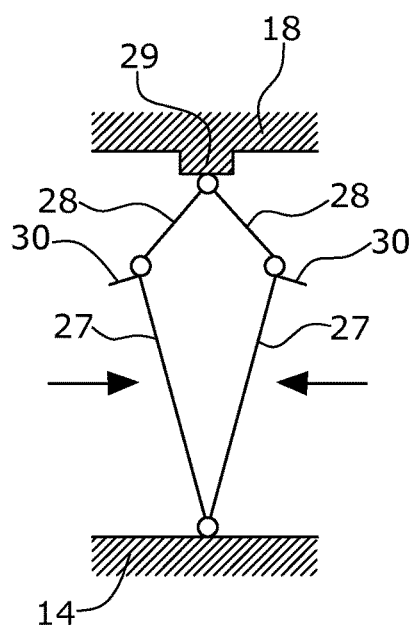
Figure 3:
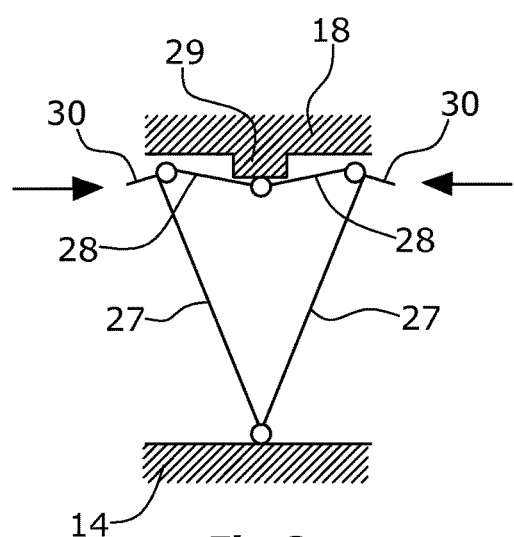
Figure 4:
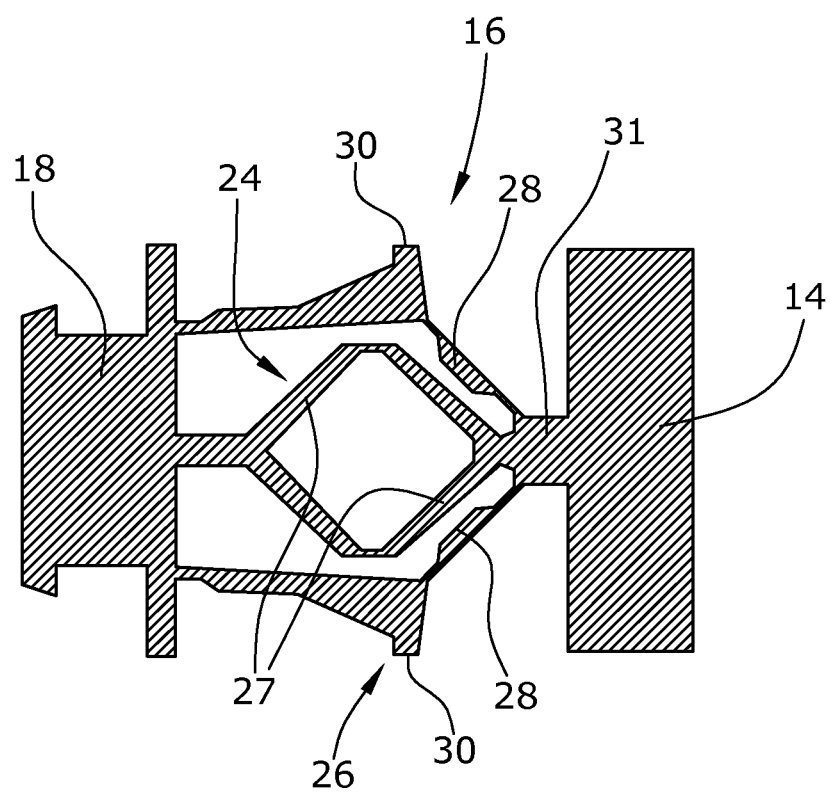

Hereunder two exemplary embodiments of the invention are described in detail with reference to the drawings in which:

FIG. 1 shows an exploded view of the inventive injection device according to the first exemplary embodiment, FIG. 2 shows a detail of FIG. 1, FIG. 3 shows a view similar to that of FIG. 2 illustrating an actuated state, and FIG. 4 shows the detail corresponding to FIGS. 2 and 3, according to the second exemplary embodiment.

The Figures show the barrel 12, the piston 14, the overpressure protection 16 and the plunger 18 of the illustrated exemplary embodiment of the injection device 10. The barrel 12 is provided with a front-end outlet 20. For illustration purposes, the outlet 20 is shown as an open front end of the barrel 12. Typically, the outlet 20 is a conventional outlet of a syringe barrel. The outlet 20 is adapted to be connected in a technically simple and conventional manner with a fluid conduction line, such as a catheter or a needle of a syringe.

The front end 22 of the barrel 12 opposite to the outlet 20 is also an open end into which the piston 14 and the plunger 18 are pushed for actuating the piston 14. Between the piston 14 and the plunger 18 the overpressure protection 16 is arranged and connected with the piston 14 and the plunger 18, respectively.

The pressure relief means 16 is made up of a sensor 24 and an actuator 26. The sensor 24 is a spring element defined by two spring legs 27 each of which is rigidly connected at a first end with the piston 14. The spring legs 27 are of the elastically bending type and form a V. The ends of the spring legs 27 at a second end facing away from the piston 14 are each articulated to a second end of a living hinge 28. Each living hinge 28 is articulated at a first end to a base 29 centrally provided at the proximal front end of the plunger 18. The actuator 26 includes a braking device made up of two braking elements 30 which are each defined at the outer ends of the spring legs 27 opposite to the piston 14. Each braking element 30 is directed laterally outwards towards the inside of the piston wall. The actuator 26 is defined by the spring element comprising the two braking elements 30 as well as the living hinges 28.

The spring element defined by the spring legs 27 has such a spring constant that the spring element is activated when a critical actuation pressure acting upon the plunger 18 of approximately 20 psi, i. e. approximately 1.4 bar, for example, is exceeded. When the spring element is activated, the living hinges 28 press the spring legs 27 outwards, as is shown in FIGS. 2 and 3. When the living hinges 28 are overstretched, the spring force, illustrated by the two arrows in FIGS. 2 and 3, presses the living hinges 28 inwards and against the base 29. In FIG. 3 the spring element is activated and retains the living hinges 28 in a stable position in which the braking elements 30 at the outer ends of the spring legs 27 press against the inner wall of the barrel 12. Here, the living hinges 28 are pivoted such that the portion of the actuation pressure coming from the living hinges 28 and acting upon the plunger 18 from the direction indicated by the arrow shown in the Figure in axial direction of the barrel 12 is transferred radially outwards to the two braking elements 30. The braking elements 30 are thereby pressed radially outwards against the inner wall of the barrel 12. In this manner, only a maximum allowable pressure is transferred from the plunger 18 to the piston 14, while an excess pressure is detected by the sensor 24 and converted via the actuator 26 into a braking force for braking and locking the piston 14. The piston 14 is friction-locked between the braking elements 30 and the inner wall of the barrel 12.

The second exemplary embodiment shown in FIG. 4 differs from the first exemplary embodiment by the configuration of the overpressure protection 16. The two braking elements 30 are each connected with a base 31 at the piston 14 via a living hinge 28. At the respective other end the braking elements 30 are each articulated to the plunger 18. The sensor of the overpressure protection 16 is a spring element defined by two spring legs 27. The spring legs 27 are connected with each other at their ends and define an O or a trapeze, as is illustrated in FIG. 4. The interconnected ends of the spring elements 27 are connected, at one side, with the base 31 at the piston 14 and, at the other side, with the plunger 18. The spring legs 27 are arranged between the two braking elements 30 and the associated living hinges 28. While in the first exemplary embodiment a spring leg 27 and a living hinge 28 are arranged in series one behind the other, the spring legs 27 and the living hinges 28 of the second exemplary embodiment are arranged side by side, wherein one braking element 30 and one living hinge 28 each are arranged in series one behind the other.

An excess pressure acting upon the plunger 18 is detected by the sensor 24 defined by the spring legs 27 and presses the spring legs 27 apart against the action of the spring force. Thereby the living hinges 28 press the braking elements 30 outwards and against the inner wall of the barrel 12 (not shown in FIG. 4). The actuator 26 defined by the braking elements 30 and the living hinges 28 converts the excess pressure acting upon the plunger 18 into a braking force for braking and locking the piston 14.

In another exemplary embodiment not shown in the Figures, the sensor may be a pressure gauge for measuring the liquid pressure in the barrel 12 or in a liquid line connected with the outlet 20. The actuator may be a valve or a diaphragm rupturing at overpressure for conducting away the excessive liquid pressure.

The invention claimed is:

1. An injection device for administering a liquid, comprising:
    a barrel having an inner wall and an outlet for the liquid;
    a piston arranged in said barrel and adapted to force the liquid out of said outlet by displacement in said barrel;
    a plunger for actuating said piston;
    an overpressure protection mechanism connected between said piston and said plunger, said overpressure protection mechanism comprising a sensor for detecting a liquid pressure in said barrel and an actuator;
    said sensor comprising a spring element rigidly connected at a first end to said piston and articulated at a second end to said actuator;
    said actuator comprising at least one living hinge coupled at a first end with said plunger and articulated at a second end to the second end of said spring element; and,
    said actuator further comprising a braking device comprising at least one braking element at the second end of said actuator for slowing a rate of advancement of said piston in said barrel;
    wherein said overpressure protection mechanism responds to the liquid pressure detected by said sensor in said barrel in excess of a critical pressure, and wherein the actuator activates the braking device to press the at least one braking element against the inner wall of the barrel to reduce the rate of advancement of said piston, whereby the braking device prevents excess pressure in the liquid forced out of said outlet.

2. The injection device according to claim 1, wherein the spring element comprises two flexible springs comprising spring legs rigidly connected at a first end to the piston.

3. The injection device according to claim 2, wherein the braking device comprises at least two braking elements, one on each side of the spring element.

4. The injection device according to claim 3, wherein the actuator comprises two living hinges.

5. The injection device according to claim 4, wherein each braking element is connected to the second end of each living hinge.

6. The injection device according to claim 3 wherein each braking element is at an outer end of a spring leg opposite to the piston.

7. The injection device according to claim 1, wherein the at least one living hinge is articulated at its first end to a base projecting from a front end of the plunger.

8. The injection device according to claim 1, wherein the sensor detects an actuation pressure applied for displacing said piston.

9. The injection device according to claim 1, wherein the sensor is a pressure gauge.

10. The injection device according to claim 1 wherein the sensor detects the liquid pressure in said barrel directly.

11. The injection device according to claim 1 wherein the sensor detects the liquid pressure in said barrel indirectly.

* * * * *